(12) United States Patent
Darnay et al.

(10) Patent No.: US 7,468,379 B2
(45) Date of Patent: Dec. 23, 2008

(54) INHIBITION OF OSTEOLYTIC LESIONS BY SRC KINASE INHIBITORS

(75) Inventors: Bryant G. Darnay, Houston, TX (US); Janet E. Price, Missouri City, TX (US); Ann Poblenz, Seattle, WA (US); Moshe Talpaz, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 106 days.

(21) Appl. No.: 11/455,272

(22) Filed: Jun. 16, 2006

(65) Prior Publication Data

US 2007/0004748 A1 Jan. 4, 2007

Related U.S. Application Data

(60) Provisional application No. 60/691,933, filed on Jun. 17, 2005.

(51) Int. Cl.
*A61K 31/47* (2006.01)
(52) U.S. Cl. ..................................... 514/313
(58) Field of Classification Search .................. 514/313
See application file for complete search history.

(56) References Cited

U.S. PATENT DOCUMENTS

| | | | | |
|---|---|---|---|---|
| 4,870,287 A | 9/1989 | Cole et al. | | 250/492.3 |
| 5,466,468 A | 11/1995 | Schneider et al. | | 424/450 |
| 5,760,395 A | 6/1998 | Johnstone | | 250/306 |
| 6,002,008 A | 12/1999 | Wissner et al. | | 546/160 |
| 2003/0212276 A1 | 11/2003 | Boschelli et al. | | 546/153 |
| 2005/0101780 A1 | 5/2005 | Boschelli et al. | | 544/363 |

OTHER PUBLICATIONS

Ammann et al., "Transgenic mice expressing soluble tumor necrosis factor-receptor are protected against bone loss caused by estrogen deficiency," *J. Clin. Invest.*, 99:1699-1703, 1997.
Blair et al., "Isolated osteoclasts resorb the organic and inorganic components of bone," *J. Cell Biol.*, 102:1164-1172, 1986.
Boschelli et al., "7-alkoxy-4-phenylamino-3-quinolinecarbonitriles as dual inhibitors of Src and Abl kinases," *J. Med. Chem.*, 47:1599-1601, 2004.
Boschelli et al., "Investigation of the effect of varying the 4-anilino and 7-alkoxy groups of 3-quinolinecarbonitriles on the inhibition of Src kinase activity," *Bioorg. Med. Chem. Lett.*, 13:3797-3800, 2003.
Boschelli et al., "Optimization of 4-phenylamino-3-quinolinecarbonitriles as potent inhibitors of Src kinase activity," *J Med. Chem.*, 44:3965-77, 2001.
Boschelli et al., "Synthesis and Src kinase inhibitory activity of a series of 4-phenylamino-3-quinolinecarbonitriles," *J Med. Chem.*, 44:822-833, 2001.
Bucay et al., "*osteoprotegerin*-deficient mice develop early onset osteoporosis and arterial calcification," *Genes Dev.*, 12:1260-1268, 1998.
Franzoso et al., "Requirement for NF-$_κ$B in osteoclast and B-cell development," *Genes & Dev.*, 11:3482-3496, 1997.
International Search Report mailed Nov. 7, 2006, (PCT/US06/23529).
Iotsova et al., "Osteopetrosis in mice lacking NF-$_κ$B1 and NF-$_κ$B2," *Nat. Med.*, 3:1285-1289, 1997.
Johnson et al., "Pleiotropic effects of a null mutation in the *c-fos* proto-oncogene," *Cell*, 71:577-586, 1992.
Kong et al., "OPGL is a key regulator of osteoclastogenesis, lymphocyte development and lymph-node organogenesis," *Nature*, 397:315-323, 1999.
Lewis et al., "Osteoporosis induced in mice by overproduction of interleukin 4," *Proc. Natl. Acad. Sci. USA*, 90:11618-11622, 1993.
Lomaga et al., "TRAF6 deficiency results in osteopetrosis and defective interleukin-1, CD40, and LPS signaling," *Genes & Dev.*, 13:1015-1024, 1999.
Mizuno et al., "Structure of the mouse osteoclastogenesis inhibitory factor (*OCIF*) gene and its expression in embryogenesis," *Gene*, 215:339-343, 1998.
Poli et al., "Interleukin-6 deficient mice are protected from bone loss caused by estrogen depletion," *EMBO J.*, 13:1189-1196, 1994.
Soriano et al., "Targeted disruption of the c-*src* proto-oncogene leads to osteopetrosis in mice," *Cell*, 64:693-702, 1991.

(Continued)

*Primary Examiner*—Raymond J Henley, III
(74) *Attorney, Agent, or Firm*—Fulbright & Jaworski, L.L.P.

(57) ABSTRACT

The present invention include methods and compositions for treating bone-resorbing diseases or bone resorption related to a pathologic condition generally, including, but not limited to osteoporosis, arthritis, rheumatoid arthritis, cancer metastases to the bone, bone cancer, hypercalcemia, osteolytic lesions with orthopedic implants, Paget's disease, and bone loss associated with hyperparathyroidism. Representative cancers include, but are not limited to breast cancer, prostrate cancer, colon cancer, endometrial cancer, multiple myeloma, renal cell carcinoma, heck and neck cancers, and cervical carcinoma. Arthritic conditions include, but are not limited to adjuvant-, collagen-, bacterial- and antigen-induced arthritis, particularly rheumatoid arthritis.

15 Claims, 8 Drawing Sheets

OTHER PUBLICATIONS

Takahashi et al., "Overexpression of the granulocyte colony-stimulating factor gene leads to osteoporosis in mice," *Lab Invest*, 74:827-34, 1996.

Ye et al., "Inhibition of Src kinase activity by 4-phenylamino-3-quinolinecarbonitriles: Optimization of the side chain at C-7," *221st National Meeting of the American Chemical Society*, San Diego, Calif., Paper 145 (Poster), Apr. 2001.

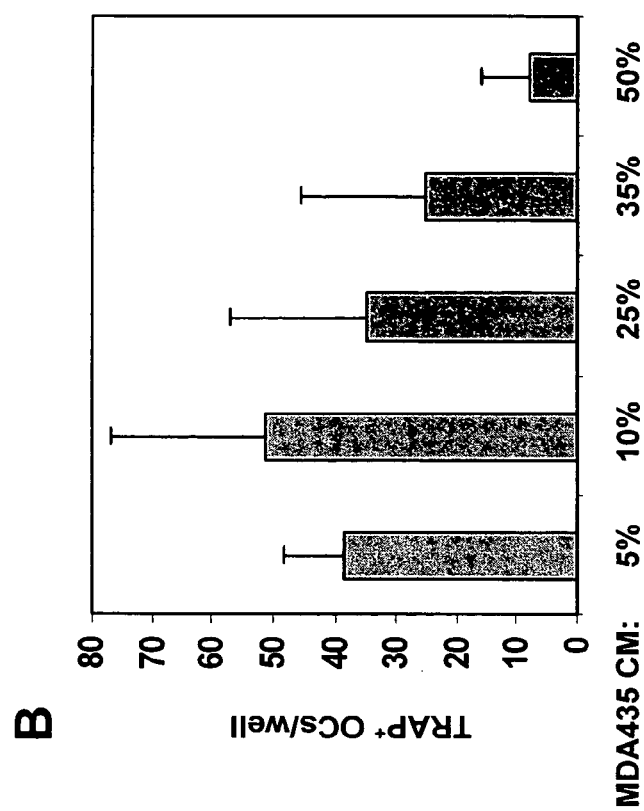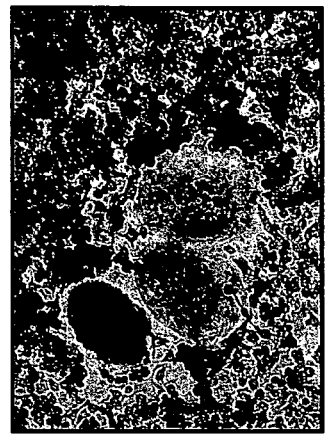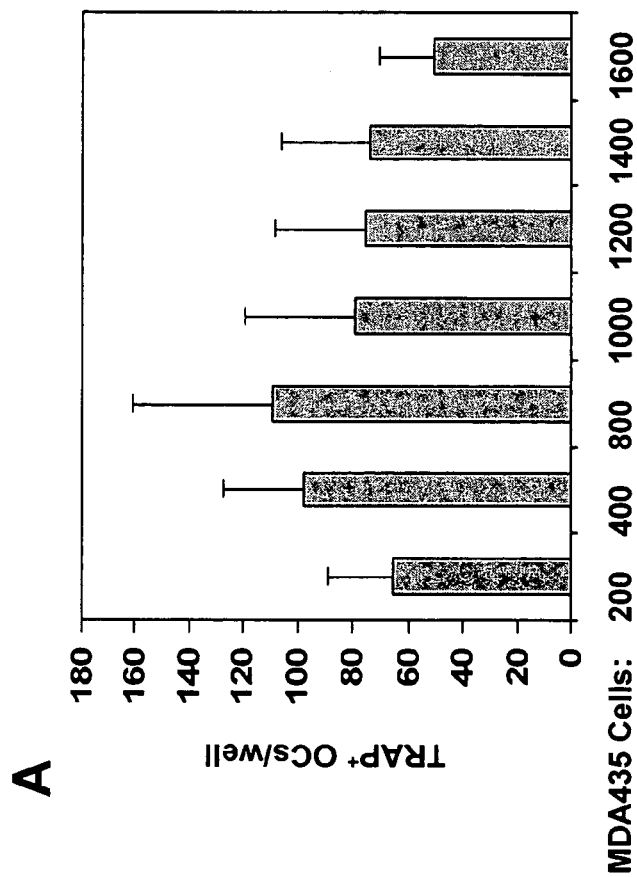
FIG 3A – 3B

INHIBITION OF OSTEOLYTIC LESIONS BY SRC KINASE INHIBITORS

This application claims priority to U.S. Provisional Patent application Ser. No. 60/691,933 filed Jun. 17, 2005, which is incorporated herein by reference in its entirety.

BACKGROUND OF THE INVENTION

I. Field of the Invention

The present invention relates generally to the field of cell biology, cell physiology, medicine, and oncology. More particularly, it concerns methods for regulating osteoclastogenesis in a subject in need thereof, and particularly osteoclastogenesis related to cancer-induced bone destruction.

II. Description of Related Art

Breast cancer is the most common female malignancy in the U.S. and is the second leading cause of cancer death in women. Women with breast cancer are at risk for bone metastases. 5 to 10% of patients with breast cancer will initially present with metastatic disease to the bone. Patients with osteolytic bone disease from metastatic breast cancer are at increased risk for pathologic fractures, bone pain, cord compression and hypercalcemia. The current standard of care for treating bone metastases is bisphosphonate therapy, which delays skeletal events, but does not completely prevent them. In addition, not all patients respond to this treatment. While a more effective treatment is desired, a further biological and molecular dissection of this disease is required. Receptor activator of NF-κB (RANK) and its ligand (RANKL, also known as TRANCE/ODF/OPGL) are essential mediators of osteoclastogenesis and have been implicated in various diseases, which include rheumatoid arthritis, osteoporosis, giant cell tumor of bone, Paget's disease, metastatic breast and prostate cancer, multiple myeloma, and familial expansible osteolysis. Osteoprotegerin (OPG, also known as OCIF/TR1) is a soluble, decoy receptor that inhibits RANKL from binding to its cell surface receptor RANK.

Knockout mouse models of RANKL, RANK, and OPG have demonstrated an essential role of these molecules in osteoclastogenesis (i.e., bone remodeling). The biological importance of these molecules is underscored by the induction of severe osteoporosis by targeted disruption of OPG and by the induction of osteopetrosis by targeted disruption of RANKL or by over expression of OPG. Thus, osteoclast formation may be attributed to the relative ratio of RANKL to OPG in the microenvironment of bone marrow, and alterations in this balance may be a major cause of bone loss in many metabolic bone disorders. Similar to RANKL -/- mice, targeted disruption of RANK also leads to an osteopetrotic phenotype. Both RANK -/- and RANKL -/- mice exhibited absence of osteoclasts, indicating the essential requirement of these molecules for osteoclastogenesis. Furthermore, RANK and RANKL are required for lymph node organogenesis and early B and T cell development. Additionally, mice lacking TRAF6, c-Src, c-Fos, or the NF-κB subunits p50/p52 also display an osteopetrotic phenotype; though these mutant mice have osteoclasts, these cells apparently have defects in bone desorption. Thus, RANKL and RANK as well as their cytoplasmic signaling molecules are the governing factors that regulate normal bone homeostasis.

The relationship between the importance of RANK/RANKL/OPG in bone remodeling and that most cancer-induced bone destruction is due to increased osteoclastic activity suggests a major role of RANK/RANKL/OPG in bone diseases and cancer. Besides the involvement of RANK/RANKL/OPG in osteoporosis, recent reports suggest a potential role of these molecules in other diseases including rheumatoid arthritis, giant cell tumor of bone, Paget's disease, and familial expansible osteolysis (due to a mutation in axon 1 of RANK). Metastatic breast and prostate cancers have the ability to invade and grow as metastases in bone causing osteolytic lesions. In metastatic tumor mouse models, in which the tumor causes increased osteoclastogenesis and bone destruction, systemic administration of OPG reduces tumor-mediated bone destruction and pain associated with bone cancer. Thus, targeting the RANK signal transduction machinery could potentially be used as a therapeutic strategy to inhibit unwanted bone destruction associated with cancer and metabolic bone disorders. Additional strategies to prevent unwanted bone destruction associated with metastatic cancers, or conditions associate with or related to bone loss are needed.

SUMMARY OF THE INVENTION

In accordance with the present invention are provided compounds of the structural Formula I, II, III, or IV:

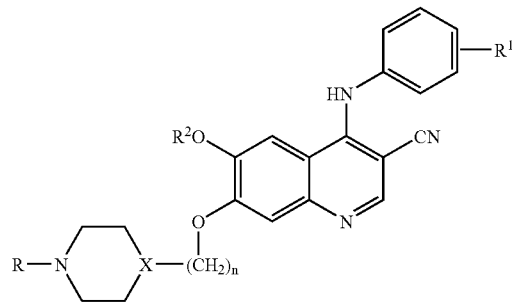

Formula I where n is an integer from 1-3; X is N, CH, provided that when X is N, n is 2 or 3; R is an alkyl of 1 to 3 carbon atoms; R(1) is 2,4-diCl, 5-OMe; 2,4-diCl; 3,4,5-tri-OMe; 2—Cl, 5-OMe; 2-Me, 5-OMe; 2,4-di-Me; 2,4-diMe-5-OMe, 2,4-diCl, 5-OEt; R(2) is an alkyl of 1 to 2 carbon atoms, and pharmaceutically acceptable salts thereof.

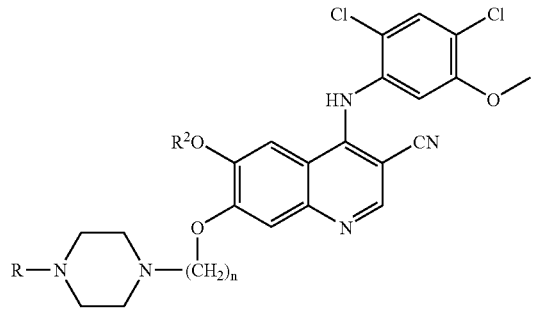

Formula II where n is 2 or 3; R is an alkyl of 1 to 3 carbon atoms; R(2) is an alkyl of 1 to 2 carbon atoms, and pharmaceutically acceptable salts thereof.

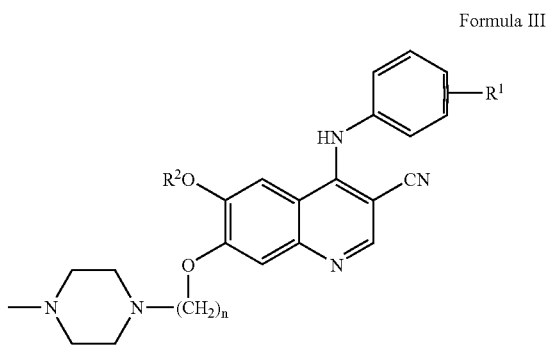

Formula III where n is 2 or 3; R(1) is 2,4-diCl, 5-OMe; 2,4-diCl; 3,4,5-tri-OMe; 2—Cl, 5-OMe; 2-Me, 5-OMe; 2,4-di-Me; 2,4-diMe-5-OMe, 2,4-diCl, 5-OEt; R(2) is an alkyl of 1 to 2 carbon atoms, and pharmaceutically acceptable salts thereof.

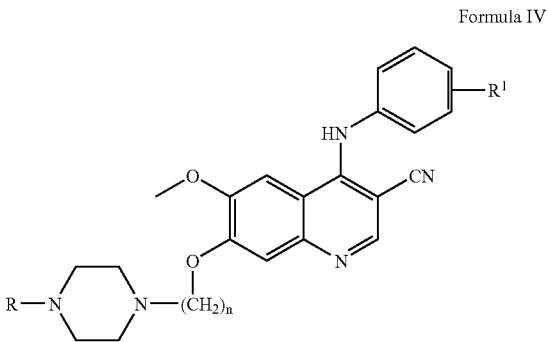

Formula IV where n is 2 or 3; R is an alkyl of 1 to 3 carbon atoms; R(1) is 2,4-diCl, 5-OMe; 2,4-diCl; 3,4,5-tri-OMe; 2—Cl, 5-OMe; 2-Me, 5-OMe; 2,4-di-Me; 2,4-diMe-5-OMe, 2,4-diCl, 5-OEt.

The compounds of this invention may be used for treating, preventing, or inhibiting bone resorption, pathological bone resorption, osteoclast activity, osteoclastogenesis, osteolytic lesions, or other pathologic conditions with associated bone loss or destruction. In certain embodiments the compounds are used as part of a pharmaceutical composition.

Specific compounds of the invention include: compound 1-4-((2,4-Dichloro-5-methoxyphenyl)amino)-6-methoxy-7-(3-(4-methyl-1-piperazinyl)propoxy)-3-quinolinecarbonitrile; compound 2-4-((2,4-Dichloro-5-methoxyphenyl)amino)-7-(3-(4-ethyl-1-piperazinyl)propoxy)-6-methoxy-3-quinolinecarbonitrile; compound 3-4-[(2,4-Dichloro-5-methoxyphenyl)amino]-6-methoxy-7-[2-(4-methyl-1-piperazinyl)ethoxy]-3-quinolinecarbonitrile; compound 4-4-[(2,4-Dichloro-5-methoxyphenyl)amino]-7-[2-(4-ethyl-1-piperazinyl)ethoxy]-6-methoxy-3-quinolinecarbonitrile; compound 5-4-[(2,4-Dichloro-5-methoxyphenyl)amino]-6-methoxy-7-[(1-methylpiperidin-4-yl)methoxy]-3-quinolinecarbonitrile; compound 6-4-[(2,4-Dichloro-5-methoxyphenyl)amino]-6-methoxy-7-[2-(1-methylpiperidin-4-yl)ethoxy]-3-quinolinecarbonitrile; compound 7-4-[(2,4-Dichloro-5-methoxyphenyl)amino]-6-methoxy-7-[3-(1-methylpiperidin-4-yl)propoxy]quinoline-3-carbonitrile; compound 8-4-[(2,4-Dichloro-5-methoxyphenyl)amino]-7-[(1-ethylpiperidin-4-yl)methoxy]-6-methoxyquinoline-3-carbonitrile; compound 9-4-[(2,4-Dichloro-5-methoxyphenyl)amino]-6-ethoxy-7-[3-(4-methylpiperazin-1-yl)propoxy]quinoline-3-carbonitrile; compound 10-4-[(2,4-Dichloro-5-methoxyphenyl)amino]-6-ethoxy-7-[(1-methylpiperidin-4-yl)methoxy]quinoline-3-carbonitrile; compound 11-4-[(2,4-Dichloro-5-methoxyphenyl)amino]-6-ethoxy-7-[3-(4-ethylpiperazin-1-yl)propoxy]quinoline-3-carbonitrile; compound 12-4-[(2,4-Dichloro-5-methoxyphenyl)amino]-6-ethoxy-7-[3-(1-methylpiperidin-4-yl)propoxy]quinoline-3-carbonitrile; compound 13-4-[(2,4-Dichloro-5-methoxyphenyl)amino]-6-ethoxy-7-[2-(4-methyl-1-piperazinyl)ethoxy]quinoline-3-carbonitrile; compound 144-[(2,4-Dichloro-5-methoxyphenyl)amino]-6-ethoxy-7-[2-(1-methylpiperidin-4-yl)ethoxy]quinoline-3-carbonitrile; compound 15-4-[(2,4-Dichloro-5-methoxyphenyl)amino]-6-methoxy-7-[3-(4-propyl-1-piperazinyl)propoxy]-3-quinolinecarbonitrile; compound 16-4-[(2,4-dichlorophenyl)amino]-6-methoxy-7-[(1-methylpiperidin-4-yl)methoxy]-3-quinolinecarbonitrile; compound 17-6-methoxy-7-[(1-methylpiperidin-4-yl)methoxy]-4-[(3,4,5-trimethoxyphenyl)amino]quinoline-3-carbonitrile; compound 18-4-[(2-chloro-5-methoxyphenyl)amino]-6-methoxy-7-[(1-methylpiperidin-4-yl)methoxy]quinoline-3-carbonitrile; compound 19-6-methoxy-4-[(5-methoxy-2-methylphenyl)amino]-7-[(1-methylpiperidin-4-yl)methoxy]quinoline-3-carbonitrile; compound 20-4-[(2,4-dimethylphenyl)amino]-6-methoxy-7-[(1-methylpiperidin-4-yl)methoxy]quinoline-3-carbonitrile; compound 21-6-methoxy-4-[(5-methoxy-2,4-dimethylphenyl)amino]-7-[(1-methylpiperidin-4-yl)methoxy]quinoline-3-carbonitrile; compound 22-4-[(2,4-dichloro-5-ethoxyphenyl)amino]-6-methoxy-7-[(1-methylpiperidin-4-yl)methoxy]quinoline-3-carbonitrile; and pharmaceutically acceptable salts thereof. In certain embodiments a preferred compound is compound 1-4-((2,4-Dichloro-5-methoxyphenyl)amino)-6-methoxy-7-(3-(4-methyl-1-piperazinyl) propoxy)-3-quinolinecarbonitrile.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternative are mutually exclusive, although the disclosure supports a definition that refers to only alternatives and "and/or."

Other objects, features, and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) The structure of the 4-phenylamino-3-quinolinecarbonitrile SKI606. (FIG. 1B) BMM cells were plated in 48 well plates ($2 \times 10^4$ cells/well) and stimulated with M-CSF (10 ng/ml) or M-CSF and RANKL (100 ng/ml), in quadruplets with indicated concentrations of SKI606. M-CSF was replenished on day 3. Cells were fixed and stained for TRAP on day five, using a TRAP staining kit from Sigma-Aldrich (St. Louis, Mo.). (FIG. 1C) Data shown is representative of three experiments. Shown are photographs of representative fields from the different treatments using a 10× objective lens.

(FIG. 2A) BMM cells were plated in 48 well plates ($2 \times 10^4$ cells/well) and pre-treated with M-CSF (10 ng/ml) or M-CSF and RANKL (300 ng/ml) in quadruplets for indicated times, then treated with 300 nM SKI606. M-CSF was replenished on day 3. Cells were fixed and stained for TRAP on day five, using a TRAP staining kit from Sigma-Aldrich (St. Louis, Mo.). (FIG. 2B) Data shown is representative of three experiments. Photographs are of representative fields from the different treatments using a 10× objective lens.

FIGS. 3A-3B. MDA-MB-435 cells stimulate osteoclastogenesis in RAW264.7 cells. (FIG. 3A) RAW264.7 cells (500 cells/well; 8 wells per treatment) were plated in 96 well plates with MDA-MD-435 cells at indicated densities and incubated for 5 days. (FIG. 3B) Conditioned media was prepared as described above. RAW264.7 cells (750 cells/well; 8 wells per treatment) incubated with conditioned media from MDA-MB-435 at indicated concentrations for 5 days. The cultures were fixed and stained for TRAP on day five, using a TRAP staining kit from Sigma-Aldrich (St. Louis, Mo.). Data shown is representative of five experiments. Photographs are of representative fields from the different treatments using a 10× objective lens.

(FIG. 4A) RAW264.7 cells (500 cells/well; 8 wells per treatment) were plated in 96 well plates with MDA-MD-435 (800 cells/well) cells at indicated densities and incubated for 5 days in the presence of increasing doses of SKI606. (FIG. 4B) RAW264.7 cells (750 cells/well; 8 wells per treatment) were plated in 96 well plates in 10% conditioned media from MDA-MB-435 for 5 days. The cultures were fixed and stained for TRAP on day five, using a TRAP staining kit from Sigma-Aldrich (St. Louis, Mo.). Data shown is representative of five experiments.

(FIG. 5A) Weight of tumor was determined as follows: weight of injected leg-weight of non-injected hind leg of the same animal. (FIG. 5B) Areas of lysis were estimated from digital X-ray images; NIH Scion program was used to measure area of tibias and lytic areas, to calculate the ratio of pixels in lytic zones/pixels in tibia area. (FIG. 5C) The tumor-injected tibia was fixed and decalcified in EDTA, and sections stained for the presence of multinucleated osteoclasts (>3 nuclei) using TRAP staining kit from Sigma-Aldrich (St. Louis, Mo.).

DESCRIPTION OF ILLUSTRATIVE EMBODIMENTS

Figures 1A, 1B, 1C:
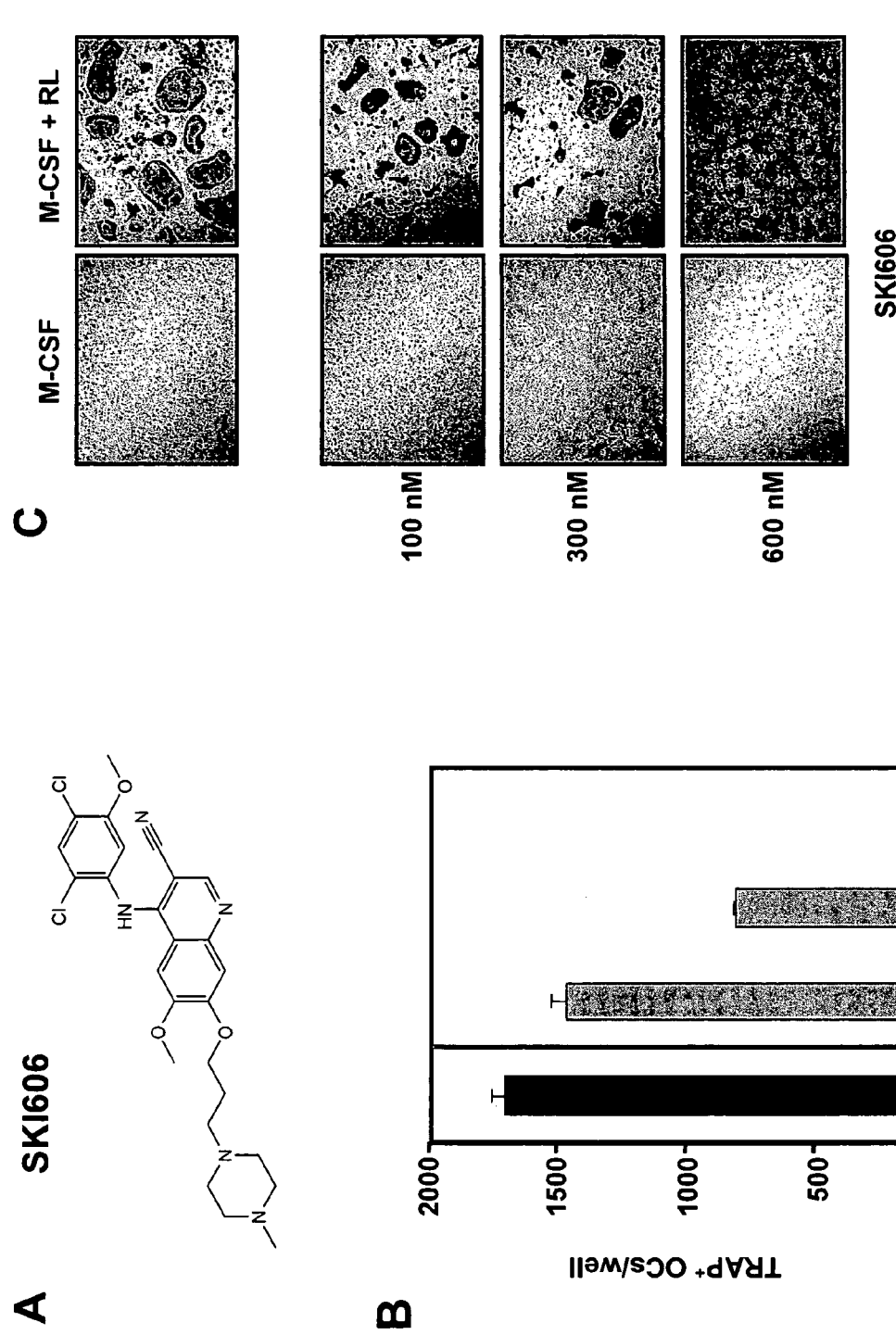
FIGS. 1A-1C. SKI606 is a potent inhibitor of osteoclastogenesis.

Living bone tissue is continuously being replenished by the process of resorption and deposition of calcium minerals. This process, described as, the absorption-resorption cycle, is facilitated by two cell types, the osteoblasts and the osteoclasts. The osteoclast is a multinucleated cell and is the only cell in the body known to have the capacity to degrade (or resorb) bone. In certain pathological conditions the absorption-resorption cycle is defective resulting in the degradation of bone. The degradation of bone typically results in an increased risk for pathologic bone fractures, bone pain, spinal cord compression and hypercalcemia.

Embodiments of the present invention include methods and compositions for treating osteolytic lesions, bone-resorbing diseases or bone resorption related to a pathologic condition, generally including, but not limited to osteoporosis, arthritis, rheumatoid arthritis, cancer metastases to the bone, bone cancer, hypercalcemia, osteolytic lesions with orthopedic implants, Paget's disease, and bone loss associated with hyperparathyroidism. Representative cancers include, but are not limited to breast cancer, prostate cancer, colon cancer, endometrial cancer, multiple myeloma, renal cell carcinoma, head and neck cancers, and cervical carcinoma. Arthritic conditions include, but are not limited to adjuvant-, collagen-, bacterial- and antigen-induced arthritis, particularly rheumatoid arthritis. Osteolytic lesions include, but are not limited to adamantinoma, aneurysmal bone cyst (lesion), angiosarcoma—high grade, angiosarcoma—low grade, bone lesions of gaucher's disease, brown tumor of hyperparathyroidism, chondroblastoma, chondromyxoid fibroma, chondrosarcoma, chordoma, clear cell chondrosarcoma, conventional intramedullary osteosarcoma, degenerative joint disease, desmoplastic fibroma, diaphyseal medullary stenosis with malignant fibrous histiocytoma, enchondroma, eosinophilic granuloma, epithelioid hemangioendothelioma, ewing's sarcoma of bone, extraosseous osteosarcoma, fibrosarcoma, fibrous dysplasia, florid reactive periostitis, giant cell tumor, glomus tumor, granulocytic sarcoma in bone, hardcastle's syndrome, hemangioma, hemangiopericytoma, high-grade surface osteosarcoma, hodgkin lymphoma of bone, intracortical osteosarcoma, intraosseous well-differentiated osteosarcoma, juxtacortical chondroma, leukemia, malignant fibrous hystiocytoma, melorheostosis, metastatic breast cancer, metastatic kidney cancer, metastatic lung cancer, metastatic prostate cancer, multifocal osteosarcoma, multiple myeloma, myositis ossificans, neurofibroma of bone, non hodgkin lymphoma, nonossifying fibroma (fibrous cortical defect), nora's lesion, osteoblastoma, osteochondroma, osteochondromatosis (hmoce), osteofibrous dysplasia, osteoid osteoma, osteoma, osteomyelitis, osteopathia striata, osteopoikilosis, osteosarcoma, paget's disease, parosteal osteosarcoma, periosteal chondroma, periosteal osteosarcoma, pigmented villonodular synovitis, post-paget's sarcoma, schwannoma of bone, small cell osteosarcoma, solitary bone cyst, solitary fibrous tumor, solitary myeloma (plasmacytoma), subchondral cyst, synovial chondromatosis, telangectatic osteosarcoma, "Tug" lesions—metaphyseal fibrous defect, or unicameral bone cyst I. SRC-Related Kinase Inhibitors In accordance with the present invention are provided compounds of the structural formula I:

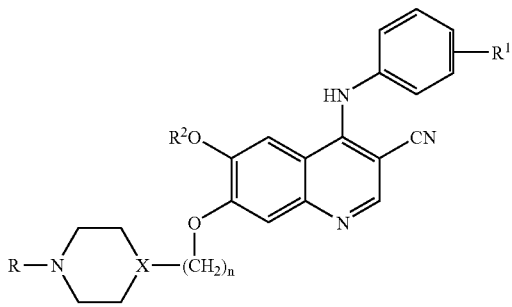

where n is an integer from 1-3; X is N, CH, provided that when X is N, n is 2 or 3; R is an alkyl of 1 to 3 carbon atoms; R(1) is 2,4-diCl, 5-OMe; 2,4-diCl; 3,4,5-tri-OMe; 2—Cl, 5-OMe; 2-Me, 5-OMe; 2,4-di-Me; 2,4-diMe-5-OMe, 2,4-diCl, 5-OEt; R(2) is an alkyl of 1 to 2 carbon atoms, and/or pharmaceutically acceptable salts thereof.

Specific compounds of the invention include: compound 1-4-((2,4-Dichloro-5-methoxyphenyl)amino)-6-methoxy-7-(3-(4-methyl-1-piperazinyl)propoxy)-3-quinolinecarbonitrile; compound 2-4-((2,4-Dichloro-5-methoxyphenyl)amino)-7-(3-(4-ethyl-1-piperazinyl)propoxy)-6-methoxy-3-quinolinecarbonitrile; compound 3-4-[(2,4-Dichloro-5-methoxyphenyl)amino]-6-methoxy-7-[2-(4-methyl-1-piperazinyl)ethoxy]-3-quinolinecarbonitrile; compound 4-4-[(2,4-Dichloro-5-methoxyphenyl)amino]-7-[2-(4-ethyl-1-piperazinyl)ethoxy]-6-methoxy-3-quinolinecarbonitrile; compound 5-4-[(2,4-Dichloro-5-methoxyphenyl)amino]-6-methoxy-7-[(1-methylpiperidin-4-yl)methoxy]-3-quinolinecarbonitrile; compound 6-4-[(2,4-Dichloro-5-methoxyphenyl)amino]-6-methoxy-7-[2-(1-methylpiperidin-4-yl)ethoxy]-3-quinolinecarbonitrile; compound 7-4-[(2,4-Dichloro-5-methoxyphenyl)amino]-6-methoxy-7-[3-(1-methylpiperidin-4-yl)propoxy]quinoline-3-carbonitrile; compound 8-4-[(2,4-Dichloro-5-methoxyphenyl)amino]-7-[(1-ethylpiperidin-4-yl)methoxy]-6-methoxyquinoline-3-carbonitrile; compound 9-4-[(2,4-Dichloro-5-methoxyphenyl)amino]-6-ethoxy-7-[3-(4-methylpiperazin-1-yl)propoxy]quinoline-3-carbonitrile; compound 10-4-[(2,4-Dichloro-5-methoxyphenyl)amino]-6-ethoxy-7-[(1-methylpiperidin-4-yl)methoxy]quinoline-3-carbonitrile; compound 11-4-[(2,4-Dichloro-5-methoxyphenyl)amino]-6-ethoxy-7-[3-(4-ethylpiperazin-1-yl)propoxy]quinoline-3-carbonitrile; compound 12-4-[(2,4-Dichloro-5-methoxyphenyl)amino]-6-ethoxy-7-[3-(1-methylpiperidin-4-yl)propoxy]quinoline-3-carbonitrile; compound 13-4-[(2,4-Dichloro-5-methoxyphenyl)amino]-6-ethoxy-7-[2-(4-methyl-1-piperazinyl)ethoxy]quinoline-3-carbonitrile; compound 14-4-[(2,4-Dichloro-5-methoxyphenyl)amino]-6-ethoxy-7-[2-(1-methylpiperidin-4-yl)ethoxy]quinoline-3-carbonitrile; compound 15-4-[(2,4-Dichloro-5-methoxyphenyl)amino]-6-methoxy-7-[3-(4-propyl-1-piperazinyl)propoxy]-3-quinolinecarbonitrile; compound 16-4-[(2,4-dichlorophenyl)amino]-6-methoxy-7-[(1-methylpiperidin-4-yl)methoxy]-3-quinolinecarbonitrile; compound 17-6-methoxy -7-[(1-methylpiperidin-4-yl)methoxy]-4-[(3,4,5-trimethoxyphenyl)amino]quinoline-3-carbonitrile; compound 18-4-[(2-chloro-5-methoxyphenyl)amino]-6-methoxy-7-[(1-methylpiperidin-4-yl)methoxy]quinoline-3-carbonitrile; compound 19-6-methoxy-4-[(5-methoxy-2-methylphenyl)amino]-7-[(1-methylpiperidin-4-yl)methoxy]quinoline-3-carbonitrile; compound 20-4-[(2,4-dimethylphenyl)amino]-6-methoxy-7-[(1-methylpiperidin-4-yl)methoxy]quinoline-3-carbonitrile; compound 21-6-methoxy-4-[(5-methoxy-2,4-dimethylphenyl)amino]-7-[(1-methylpiperidin-4-yl)methoxy]quinoline-3-carbonitrile; compound 22-4-[(2,4-dichloro-5-ethoxyphenyl)amino]-6-methoxy-7-[(1-methylpiperidin-4-yl)methoxy]quinoline-3-carbonitrile; and pharmaceutically acceptable salts thereof.

The compounds of this invention may be used for treating, ameliorating, preventing, or inhibiting osteoclastogenesis or bone loss. In a preferred embodiment the compounds are used as part of a pharmaceutical composition. In a preferred embodiment, compound 1-4-((2,4-Dichloro-5-methoxyphenyl)amino)-6-methoxy-7-(3-(4-methyl-1-piperazinyl)propoxy)-3-quinolinecarbonitrile is used in inhibiting osteoclastogenesis or bone loss.

Pharmaceutically acceptable salts are those derived from such organic and inorganic acids as: acetic, lactic, carboxylic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In a preferred embodiment, a straight chain or branched chain alkyl has 3 or fewer carbon atoms in its backbone.

The compounds may be provided by oral; intralesional; intraperitoneal; intramuscular or intravenous injection; infusion; liposome-mediated delivery; topical; nasal; anal; vaginal; sublingual; uretheral; transdermal; intrathecal; ocular or otic delivery. In order to obtain consistency in providing the compound of this invention it is preferred that a compound of the invention is in the form of a unit dose. Suitable unit dose forms include tablets, capsules and powders in sachets or vials. Such unit dose forms may contain from 0.1, 0.5, 1, 10, 100, 200 to 300 ng or mg of a compound of the invention, including all values and ranges there between, and in certain aspects from 2 to 100 ng or mg. In another embodiment the unit dosage forms contain 50 to 150 mg of a compound of the present invention. The compounds of the present invention can be administered orally or by other well known routes of administration. Such compounds may be administered from 1, 2, 3, 4, 5 to 6 times a day, more usually from 1, 2, 3, to 4 times a day, week or month, over weeks, months or years. The effective amount will be determinable by one of skill in the art; it will also be dependent upon the form of the compound. One of skill in the art could routinely perform empirical activity tests to determine the bioactivity of the compound in bioassays and thus determine what dosage to administer, as well as extrapolating and analyzing clinical trial data.

The compounds of the invention may be formulated with conventional excipients, such as a filler, a disintegrating agent, a binder, a lubricant, a flavoring agent, a color additive, or a carrier. The carrier may be for example a diluent, an aerosol, a topical carrier, an aqueous solution, a nonaqueous solution or a solid carrier. The carrier may be a polymer. A carrier in this invention encompasses any of the standard pharmaceutically accepted carriers, such as phosphate buffered saline solution, acetate buffered saline solution, water, emulsions such as an oil/water emulsion or a triglyceride emulsion, various types of wetting agents, tablets, coated tablets and/or capsules.

When provided orally or topically, such compounds would be provided to a subject by delivery in different carriers. Typically, such carriers contain excipients such as starch, milk, sugar, certain types of clay, gelatin, stearic acid, talc, vegetable fats or oils, gums, or glycols. The specific carrier would need to be selected based upon the desired method of delivery, for example, phosphate buffered saline (PBS) could be used for intravenous or systemic delivery and vegetable fats, creams, salves, ointments or gels may be used for topical delivery.

The compounds of the present invention may be delivered together with suitable diluents, preservatives, solubilizers, emulsifiers, adjuvants and/or carriers useful in treatment or prevention of an osteolytic lesion and/or bone loss. Such compositions are liquids or lyophilized or otherwise dried formulations and include diluents of various buffer content (for example, Tris-HCl, acetate, phosphate), pH and ionic strength, additives such as albumins or gelatin to prevent absorption to surfaces, detergents (for example, TWEEN 20, TWEEN 80, PLURONIC F68, bile acid salts), solubilizing agents (for example, glycerol, polyethylene glycerol), antioxidants (for example ascorbic acid, sodium metabisulfate), preservatives (for example, thimerosal, benzyl alcohol, parabens), bulking substances or tonicity modifiers (for example, lactose, mannitol), covalent attachment of polymers such as polyethylene glycol, complication with metal ions, or incorporation of the compound into or onto particulate preparations of hydro gels or liposomes, micro-emulsions, micelles, unilamellar or multilamellar vesicles, erythrocyte ghosts, or spheroblasts. Such compositions will influence the physical state, solubility, stability, rate of in vivo release, and rate of in vivo clearance of the compound or composition. The choice of compositions will depend on the physical and chemical properties of the compound capable of treating, ameliorating or preventing a particular condition or disease state.

The compound of the present invention may be delivered locally via a capsule that allows a sustained release of the compound over a period of time. Controlled or sustained release compositions include formulation in lipophilic depots (for example, fatty acids, waxes, oils).

The present invention further provides a compound of the invention for use as an active therapeutic substance for treating, regulating, ameliorating, preventing, or inhibiting osteoclastogenesis or bone loss.

The present invention further provides a method of treating bone loss in humans, which comprises administering to the individual, diagnosed with or at risk of developing an osteolytic lesion, an effective amount of a compound or a pharmaceutical composition of the invention. The dose provided to a patient will vary depending upon what is being administered, the purpose of the administration, the manner of administration, and the like. A "therapeutically effective amount" is an amount sufficient to cure, reduce or ameliorate symptoms of bone loss.

The compounds of the invention may be delivered alone or in combination with other compounds used to treat any related disease state or pathologies.

The compounds of this invention were prepared from: (a) commercially available starting materials (b) known starting materials which can be prepared as described in the literature or (c) new intermediates described in the schemes and experimental procedures referenced herein. Compounds included in this invention can be prepared according to the synthesis routes disclosed in U.S. Pat. Nos. 6,002,008 and 6,780,996; and U.S. Patent Application 20050101780A1, which are each incorporated herein by reference in their entireties.

Reactions are performed in a solvent appropriate to the reagents and materials employed and suitable for the reactions being effected. It is understood by those skilled in the art of organic synthesis that the various functionalities present on the molecule must be consistent with the chemical transformations proposed. When not specified, order of synthetic steps, choice of protecting groups and deportation conditions will be readily apparent to those skilled in the art. In addition, in some instances, substituents on the starting materials may be incompatible with certain reaction conditions. Restrictions pertinent to given substituents will be apparent to one skilled in the art. Reactions are run under inert atmospheres where appropriate.

The preparation of compounds of Formula I have been reported in the literature, (Boschelli et al., 2001a; Boschelli et al., 2001b; Boschelli et al., 2003; Boschelli et al., 2004, and Ye et al., 2001, each of which is incorporated herein by reference).

II. Bone Absorption-Resorption Cycle

Living bone tissue is continuously being replenished by the process of resorption and deposition of calcium minerals. This process, described as, the absorption-resorption cycle, is facilitated by two cell types, the osteoblasts and the osteoclasts. The osteoclast is a multinucleated cell and is the only cell in the body known to have the capacity to degrade (or resorb) bone. This resorption activity is accomplished by the osteoclast forming pits (resorption lacunae) in bone tissue. In fact, osteoclast activity in cell culture is measured by their capacity to form these pits on slices of mineralized tissue such as bone or sperm whale dentine. The osteoclast is derived from a hematopoietic precursor which it shares with the formed elements of the blood (Takahashi et al., 1987). The precursor for the osteoclast is a mononuclear cell (cell with a single nucleus) which is found in the bone marrow and which forms the mature and unique multinucleated osteoclast after undergoing replication and differentiation by means of cell fusion. The mature osteoclast is distinguished from other multinucleated cells by the presence of the enzyme tartrate-resistant acid phosphatase (TRAP) which is often used as an osteoclast cell marker.

Among the pathological conditions associated with an abnormal osteoclast development or function are conditions wherein increased bone resorption results in the development of fragile and/or brittle bone structure, such as osteoporosis, or increased bone absorption results in the development of excess bone mass, such as osteopetrosis. It is believed that the development of excess or deficient populations of osteoclasts or osteoblasts results from a corresponding lack or excess of specific cytokines.

Many of the known cytokines stimulate or inhibit blood cells: Several growth regulatory cytokines such as M-CSF, transforming growth factor alpha (TGF-α), interleukin-1 (IL-1) and tumor necrosis factor (TNF) have been shown to stimulate marrow mononuclear cell proliferation. Although cytokines such as interleukin-1, tumor necrosis factor and interleukin-6 (IL-6) may influence osteoclast formation and differentiation (Mundy, 1990), these factors are not specific osteoclast growth regulatory factors.

Knockout mouse models of RANKL, RANK, and osteoprotegerin decoy receptor (OPG) have demonstrated an essential role of these molecules in osteoclastogenesis (i.e., bone remodeling). The biological importance of these molecules is underscored by the induction of severe osteoporosis by targeted disruption of OPG and by the induction of osteopetrosis by targeted disruption of RANKL or by over expression of OPG (Bucay et al., 1998; Kong et al., 1999; Mizuno et al., 1998). Thus, osteoclast formation may be attributed to the relative ratio of RANKL to OPG in the microenvironment of bone marrow, and alterations in this balance may be a major cause of bone loss in many metabolic bone disorders. Similar to RANKL −/− mice, targeted disruption of RANK also leads to an osteopetrotic phenotype (Dougall et al., 1999; Li et al., 2000). Both RANK −/− and RANKL −/− mice exhibited absence of osteoclasts, indicating the essential requirement of these molecules for osteoclastogenesis. Furthermore, RANK and RANKL are required for lymph node organogenesis and early B and T cell development (Dougall et al., 1999; Kong et al., 1999). Additionally, mice lacking TRAF6 (Lomaga et al., 1999), c-Src (Soriano et al., 1991), c-Fos (Johnson et al., 1992), or the NF-κB subunits p50/p52 (Franzoso et al., 1997; Iotsova et al., 1997) also display an osteopetrotic phenotype; though these mutant mice have osteoclasts, these cells apparently have defects in bone resorption.

Maintenance of bone integrity requires a dynamic balance between bone formation and bone resorption. The net pool size of active osteoclasts is determined by the net effects of differentiation and fusion of osteoclast precursors and by the activity and rate of apoptosis of active osteoclasts. Although various cytokines (TNF, IL-1, IL-6, IL-11, TGFα) and molecules (11α, 25-dihydroxyvitamin D3 and glucocorticoids) expressed by osteoblast lineage cells have been shown to play a role in osteoclast differentiation, it appears that the essential factors are RANKL (produced by osteoblasts) and RANK (expressed on osteoclasts and osteoclast progenitors), as well as the resultant intracellular signaling mechanisms and pathways. There is also a requirement for M-CSF, but its function still remains elusive, but is probably only required for the initiation of differentiation of the early osteoclast progenitors and survival.

The human skeleton is continuously remodeled, normally turning over in about 2 years and allows use of skeletal mineral in calcium homeostasis. The strength and shape of the skeleton is preserved by segmental replacement: a bone section is degraded by osteoclasts, formed from monocyte-macrophage precursors (Scheven et al., 1986; and Fujikawa et al., 1996), while osteoblasts, derived from stromal cells, synthesize new bone (Rickard, et al, 1996). These unrelated cells differentiate in a coupled manner, producing a new bone section in a few weeks.

Osteoclasts, which are multinucleated giant cells, arise from hematopoietic stem cells and are the primary cells responsible for physiological and pathological bone resorption. Osteoclasts are specialized for the removal of both the inorganic and organic phases of bone (Blair et al., 1986). Changes in the levels of cytokines and growth factors in bone microenvironment cause abnormal bone resorption by the osteoclasts (for a review see Mundy, et al., 1997). Accordingly, forced expression of IL-4 (Lewis, et al., 1993), and G-CSF (Takahashi, et al., 1996) in mice induced osteopenia, while mice over expressing soluble TNF-α receptor (Amman, et al., 1997) or depleted of the IL-6 gene (Poli, et al., 1994) are protected against bone loss caused by estrogen deficiency.

Dissolution of the hydroxyapatite mineral phase is dependent upon acidification of the subosteoclastic resorption lacuna, via the action of carbonic anhydrase II and a proton pump (Vaes, 1968; Baron et al., 1985; Blair et al., 1992).

Excessive bone resorption by osteoclasts contributes to the pathology of many human diseases including arthritis, osteoporosis, periodontitis, and hypercalcemia of malignancy. During resorption, osteoclasts remove both the mineral and organic components of bone (Blair et al., 1986). The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid treatment. All these conditions are characterized by bone loss, resulting from an imbalance between bone resorption (breakdown) and bone formation, which continues throughout life at the rate of about 14% per year on the average. However, the rate of bone turnover differs from site to site, for example it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk. Turnover may be effected by an increase or decrease in osteoblast activity or an increase or decrease in osteoclast activity. Compositions and methods for modulating osteoclast and/or osteoblast in a subject would be useful in the treatment of a variety of diseases or conditions associated with bone loss.

All the conditions listed above would benefit from treatment with agents which inhibit or regulate osteoclastogenesis or bone resorption. One mechanism for the inhibition of bone resorption is the inhibition of osteoclast precursor cell fusion.

III. Methods for Treating Osteolytic Conditions

The present invention involves the treatment of subjects with a pathological bone restoration malady or condition. The term "therapeutic benefit" refers to anything that promotes or enhances the well-being of the subject with respect to the medical treatment of his/her condition, which includes treatment of osteolytic conditions and/or regulation of bone resorption, osteoclast activity, and/or osteoclastogenesis.

A. Pharmaceutical Formulations and Delivery

In certain embodiments of the present invention, methods involving delivery of one or more compounds of the invention are contemplated. Examples of diseases and conditions that may be prevented, ameliorated, or treated with one or more compound of the invention include bone loss associate with cancer metastasis to the bone, which includes, but is not limited to lung, head and neck, breast, pancreatic, prostate, renal, bone, testicular, cervical, gastrointestinal, colon, bladder and other cancer metastases, as well as other diseases or condition related to or associated with osteolytic lesions.

An "effective amount" of the pharmaceutical composition, generally, is defined as that amount sufficient to detectably and repeatedly to achieve the stated desired result, for example, to ameliorate, reduce, minimize or limit the extent of the osteolytic condition or disease, or its symptoms. In certain aspects, more rigorous definitions may apply, including prevention, elimination, eradication or cure of disease.

In certain specific embodiments, it is desired to inhibit osteoclastogenesis or otherwise reverse, hinder or reduce the resorption of bone using the methods and compositions of the present invention. The routes of administration will vary, naturally, with the location and nature of the lesion and may include, for example, intradermal, subcutaneous, regional, parenteral, intravenous, intramuscular, intranasal, systemic, and oral administration and formulation.

Continuous administration also may be applied where appropriate. Delivery via syringe or catherization is contemplated. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time. Unit dose of the present invention may conveniently be described in terms of mg per volume of formulation or weight (e.g., milligrams or mg) of therapeutic composition.

In some embodiments, the method for the delivery of a composition comprising one or more compositions of the invention is via systemic administration. However, the pharmaceutical compositions disclosed herein may alternatively be administered parenterally, subcutaneously, intratracheally, intravenously, intradermally, intramuscularly, or even intraperitoneally. Injection may be by syringe or any other method used for injection of a solution.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi.

The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media which can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the some methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

B. Combination Treatments

In certain embodiments, the compositions and methods of the present invention involve a compound inhibiting or regulating bone resorption, osteoclast activity, and/or osteoclastogenesis, which in turn may be used in combination with other agents or compositions to enhance the effect of other treatments, such as anti-neoplastic treatments, to better the quality of life of a subject being treated. These compositions would be provided in a combined amount effective to achieve the desired effect, for example, the killing or growth inhibition of a cancer cell and the inhibition of osteoclasotgenesis, the activity of osteoclasts, or the resorption of bone. This process may involve contacting the cells with a composition of the invention, and a second therapeutic agent(s) or multiple factor(s) at the same time. This may be achieved by contacting the cell with a single composition or pharmacological formulation that includes two or more agents, or by contacting the cell with two or more distinct compositions or formulations wherein at least one composition includes a composition of the invention and one or more other compositions includes at least a second therapeutic agent.

In one embodiment of the present invention, it is contemplated that anti-osteoclast therapy is used in conjunction with immune therapy intervention, in addition to pro-apoptotic, anti-angiogenic, anti-cancer, or cell cycle regulating agents. Alternatively, the therapy may precede or follow the other agent treatment by intervals ranging from minutes to weeks. In embodiments where one or more second therapeutic agent and an anti-osteoclast therapy are applied separately to a cell, tissue, organ or subject, one would generally ensure that a significant period of time did not expire between the time of each delivery, such that the second agent and the inventive composition would still be able to exert an advantageously combined effect on the subject. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, for example a composition of the present invention is "A" and a second therapy, such as chemotherapy, is "B":

A/B/A B/A/B B/B/A A/A/B A/B/B B/ A/A A/B/B/B B/A/ B/B

B/B/B/A B/B/A/B A/A/B/B A/B/A/B A/B/B/A B/B/A/A B/A/B/A B/A/A/B A/A/A/B B/A/A/A A/B/A/A A/A/B/A

Administration of the anti-osteoclast compositions of the present invention to a patient will follow general protocols for the administration of such compositions, taking into account the toxicity, if any. It is expected that the treatment cycles would be repeated as necessary. It also is contemplated that various standard therapies, as well as surgical intervention, may be applied in combination with the described therapy.

In specific embodiments, it is contemplated that an anti-cancer therapy, such as chemotherapy, radiotherapy, or immunotherapy, is employed in combination with the anti-osteoclast therapies described herein.

1. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves, proton beam irradiation (U.S. Pat. No. 5,760,395 and U.S. Pat. No. 4,870,287) and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic composition and a chemotherapeutic or radiotherapeutic agent are delivered to a target cell, tissue or subject, or are placed in direct juxtaposition.

3. Immunotherapy

In the context of cancer treatment, immunotherapeutics, generally, rely on the use of immune effector cells and molecules (e.g., monoclonal antibodies) to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, racing A chain, cholera toxin, peruses toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993). In melanoma immunotherapy, those patients who elicit high IgM response often survive better than those who elicit no or low IgM antibodies (Morton et al., 1992). IgM antibodies are often transient antibodies and the exception to the rule appears to be anti-ganglioside or anti carbohydrate antibodies.

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this, one would administer to an animal, or human patient, an immunologically effective amount of activated lymphocytes in combination with an adjuvant-incorporated antigenic peptide composition as described herein. The activated lymphocytes will most preferably be the patient's own cells that were earlier isolated from a blood or tumor sample and activated (or "expanded") in vitro. This form of immunotherapy has produced several cases of regression of melanoma and renal carcinoma, but the percentage of responders were few compared to those who did not respond.

4. Surgery

Approximately 60% of persons with cancer will undergo surgery of some type, which includes preventative, diagnostic or staging, curative and palliative surgery. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electro surgery, and microscopically controlled surgery (Mohs' surgery). It is further contemplated that the present invention may be used in conjunction with removal of superficial cancers, precancers, or incidental amounts of normal tissue.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods

Animals and cell lines. Female athymic NCr nude mice were obtained from the Animal Production Area of the National Cancer Institute, Frederick Cancer Research Facility (Frederick, MD). Black 6 mice (C57BL/6J) were obtained from Charles Rivers (Wilmington, Mass.). The mice were maintained in a laminar air-flow cabinet under specific pathogen-free conditions and used at 8 weeks of age. All facilities were approved by the American Association for Accreditation of Laboratory Animal Care (AAALAC) in accordance with the current regulations and standards of the United States Department of Agriculture, the Department of Health and Human Services, and the NIH. Mice were fed with Purina rodent chow and tap water ad libitum. The breast cancer cell line, MDA-MB-435 cells were maintained in D-MEM (Invitrogen, Carlsbad, Calif.) supplemented with 10% FBS and 1 mM sodium private (Invitrogen, Carlsbad, Calif.). The mouse macrophage cell line RAW264.7 was maintained in DMEM/F12 (Invitrogen, Carlsbad, Calif.) supplemented with 10% FBS (Invitrogen, Carlsbad, Calif.). All media contained Fungizone at a 1:100 dilution (final concentration: penicillin G, streptomycin at 100 units/ml and amphotericin B 250 ng/ml).

Primary Bone Marrow Cell Culture. Primary bone marrow cells (BMM) from the tibiae and femora were aseptically dissected from Black 6 mice (C57BU6J) 8-12 weeks of age. Bone marrow was flushed out with incomplete D-MEM and centrifuged at 1200 rpm for 3 minutes and re-suspended in 5 ml incomplete D-MEM. BMM cells were incubated in 20 ml Red Blood Cell lysis buffer (8.3 g/$NH_4Cl$, 1 g/l sodium bicarbonate, 0.4 g/l EDTA) at room temperature for 1-2 min. 25 ml of D-MEM supplemented with 10% FBS and 100 units/ml penicillin (complete D-MEM) were added and BMM cells were centrifuged for 3 min at 1200 rpm. BMM cells were then plated at $1.5-2 \times 10^7$ cells/10 cm dish with 10 ml of complete D-MEM and cultured for 24 h. Non-adherent cells were collected and centrifuged for 5 min at 1200 rpm and plated at a concentration of $2.5 \times 10^4$ cells/well in a 96 well dish for cytotoxicity assay, $2 \times 10^4$ cells/well in 48-well plates, or $5 \times 10^3$ cells/well in 96-well plates for osteoclast differentiation assays. Cells were cultured for 3 days in the presence of 10 ng/ml M-CSF before they were washed and used for further studies. For differentiation into osteoclasts 30-100 ng/ml RANKL is added. Media was supplemented after 2 days with fresh M-CSF and RANKL.

Cytotoxicity Assay. Cytotoxicity of SKI606 against BMM cells was performed in 96-well flat-bottom tissue culture dishes. BMM cells ($2.5 \times 10^4$) were plated and treated as described above. SKI606 was diluted in culture media and added to the wells in 2-fold serial dilutions. Cells were incubated for 72 h and the remaining adherent cells were stained with crystal violet (0.5% in 20% methanol) and solubilized with Sorenson's buffer (0.1 M sodium citrate, pH 4.2, in 50% ethanol). Absorbance was measured at 630 nm using an EL800 universal microplate reader from Bio-Tek Instruments Inc (Winooski, Vt.).

In Vitro Osteoclast Differentiation. BMM cells ($2 \times 10^4$) were cultured in 48-well plates as described above and then treated with 100 ng/ml RANKL and 10 ng/ml M-CSF. Cell cultures were subject to a medium change on day 3. At day 5, cells were fixed and assessed for osteoclast differentiation by counting the total number of TRAP-positive, multinucleated (>3 nuclei), cells per well 96 h post-treatment using Leucocyte Acid phosphatase kit from Sigma-Aldrich (St. Louis, Mo.).

Bone-Resorption Assay. BMM cells ($5 \times 10^3$) were cultured in 96-well plates as described above. In short, cells were seeded onto OsteoAssay™ plates from Cambrex (Rockland, Me.) and initially treated with 100 ng/ml RANKL and 10 ng/ml M-CSF with or without 300 nM SKI606. Cell cultures were supplemented with fresh 10 ng/ml M-CSF at day three. On day 5, a 201l1 aliquot of the supernatant was used to evaluate the bone resorption from the OsteoAssay™ plate. Bone resorption was evaluated by measuring collagen I release from the OsteoAssay plate using Cross Laps for Culture ELISA kit from Nordic Bioscience Diagnostics (Portsmouth, Va.). Absorbance was measured at 450 nm using the reading at 650 nm as reference using an EL800 universal microplate reader from Bio-Tek Instruments Inc (Winooski, Vt.).

Time-dependency. BMM cells ($2 \times 10^4$) were cultured in 48-well plates as described above and treated with RANKL (100 ng/ml) in the absence or presence of 300 nM SKI606 added either with RANKL stimulation and TRAP stained at 96 h post-treatment, or added 12, 24 or 48 hours post-RANKL stimulation and TRAP stained at 96 h. Cells were then fixed, stained for TRAP and the numbers of osteoclasts were counted in each condition as described above.

RAW 264.7 Co-culture with MDA MB435 cells and Conditioned Media. For co-culture assays RAW264.7 (500 cells/well) were plated in 96 well plates and allowed to adhere for 12 hours. MDA-MB-435 were then introduced into the RAW264.7 culture at increasing density and incubated for 12 hours. Co-cultures were then incubated with or without SKI606 at indicated concentrations for 5 days. Cells were then fixed, stained for TRAP and the numbers of osteoclasts were counted in each condition as described above.

For conditioned media the MDA-MB-435 cells were plated in 10 cm plates ($1 \times 10^6$ cells/plate) and incubated for 36 hours. Media was then removed, centrifuged for 5 minutes at 2500 rpm and supernatants were isolated and placed in 4° C.

until use. RAW264.7 cells (750 cells/well) were plated in 96 well plates and allowed to adhere for 12 hours. Conditioned media from MDA-MB-435 cells was added and incubated with or SKI606 at indicated concentrations for 5 days. Cells were then fixed, stained for TRAP and the numbers of osteoclasts were counted in each condition as described above.

Intrabone Injections and Processing of Bone Tissue Samples. MDA-MB-435 cells were harvested with 0.025% trypsin-0.01% EDTA solution were washed in PBS and resuspended in PBS in preparation for implantation into the mice. Animals were anesthetized with intramuscular injections of ketamine (100 mg/kg) plus acepromazine (2.5 mg/kg). Female athymic NCr nude mice were injected with $5 \times 10^5$ MDA-MB-435 breast cancer cells in 0.01 ml of PBS, into the proximal tibia of each mouse using a 28-gauge Hamilton needle. Three days after injection the mice were divided into 3 groups and treatment started, of daily oral gavage of vehicle (0.5% Methocel/0.4% Tween in PBS), 150 mg/kg SKI606 in vehicle, or S.C. injections of 10 µg/kg Zomeda (zolendronic acid) in 0.1 ml PBS. Treatment was given daily, 5 days per week for 9 weeks. X-ray images were taken at 35 days after injection, and also at 14 days intervals. After 9 weeks, final X-ray images were taken, tumor weight calculated from the difference in weight of the tumor-bearing and non tumor-bearing leg of the same animal. The tumor-injected tibia was fixed and decalcified in EDTA, and sections stained for the presence of multinucleated osteoclasts (>3 nuclei) using Leucocyte Acid phosphatase kit from Sigma-Aldrich (St. Louis, Mo.). Incidence of tumor in the tibia was determined by examination of histology sections. Weight of tumor was determined as follows: weight of injected leg-weight of non-injected hind leg of the same animal. Areas of lysis were estimated from digital X-ray images; NIH Scion program was used to measure area of tibias and lytic areas, to calculate the ratio of pixels in lytic zones/pixels in tibia area.

Results

To identify potential kinase inhibitors, compounds 1, 2, 3, 4, and 5 were tested for their ability to inhibit RANKL-induced osteoclast differentiation of RAW264.7 cells. SKI606 was chosen because a related compound has been shown to be a dual inhibitor of Src and Abl kinases (Boschelli et al., 2001b). SKI606 was identified and characterized and it was found that this compound inhibits Src in an enzyme assay with an $IC_{50}$ of 1.2 nM and inhibits Src-dependent protein tyrosine phosphorylation at comparable concentrations.

Figures 2A, 2B:
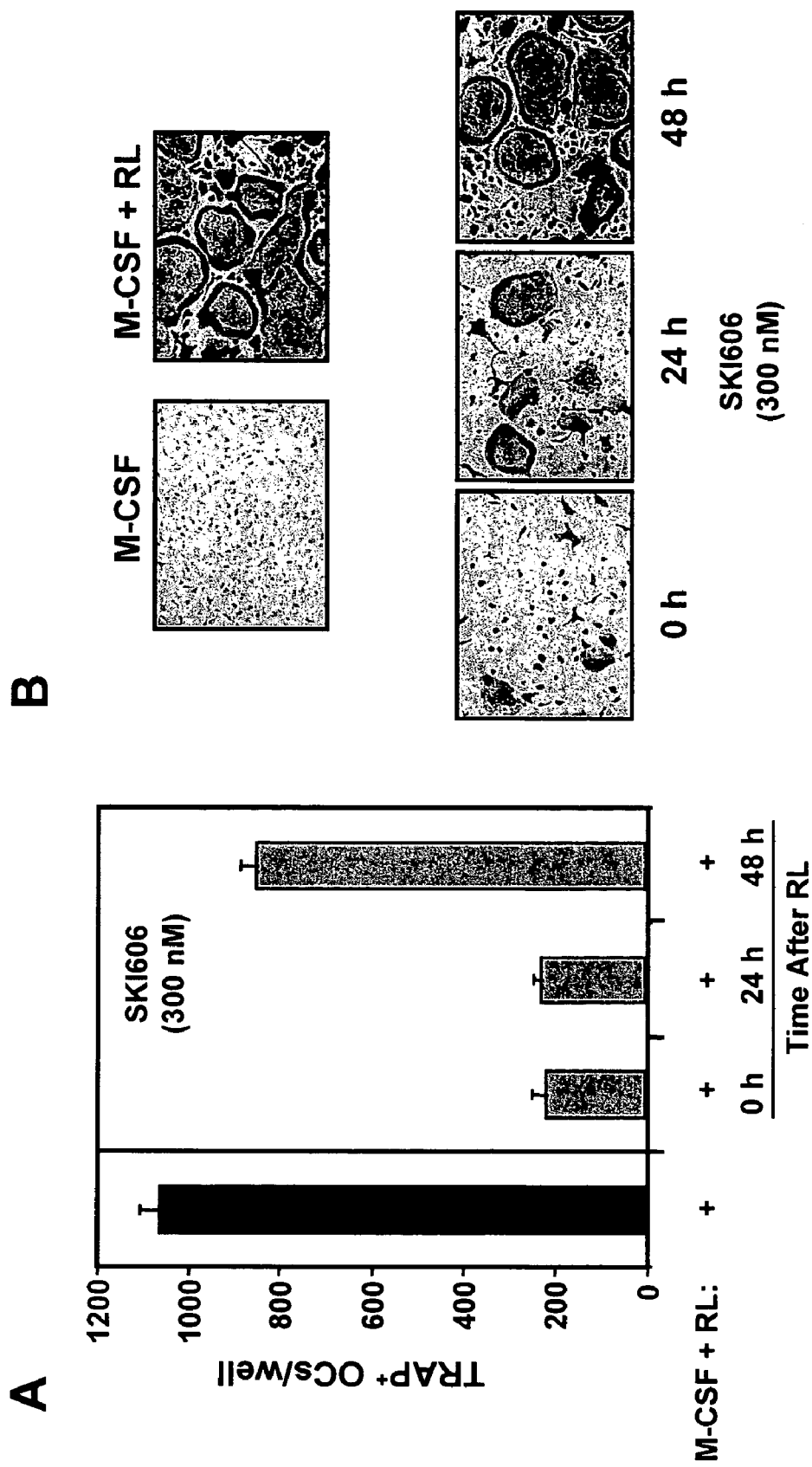
FIGS. 2A-2B. BMM cells respond to SKI606 in a time-dependent manner.

The compound is not cytotoxic to BMM cells and less than 10% of the cells died at 600 nM SKI606, indicating that the inhibitory effect on osteoclastogenesis is not due to cytotoxic activity of SKI606 on the precursor cells. The structure of this 4-pheylamino-3-quinolinecarbonitrile is known (FIG. 1A) and has an inhibitory effect on RANKL-mediated osteoclast differentiation in BMM in a dose dependent manner (FIG. 1B). BMM cells appear to be less sensitive to SKI606 if added after initiation of osteoclastogenesis (FIGS. 2A and 2B). In addition, the ability of SKI606 to inhibit bone resorption was studied by stimulating BMM cells with RANKL on OsteoAssay™ plates from Cambrex (Rockland, Me.) with or without SKI606. BMM cultures treated with M-CSF and RANKL in the presence of 300 nM SKI606 exhibited a 3.7-fold decrease in collagen I release, an indicator of bone resorption, as compared to M-CSF and RANKL treatment.

The ability of the breast cancer cell line; MDA-MB-435 to induce osteoclastogenesis in RAW264.7 cells was examined. This was found to be density-dependent with an optimal number of 800 MDA-MB-435 cells/well (FIG. 3A). The optimal number of RAW264.7 cells was established, for this study to be 500 cells/well for co-culture with MDA-MB-435 cells (data not shown). Conditioned media from MDA-MB-435 cells were also able to support osteoclastogenesis in RAW264.7 cell cultures with an optimal mixture of 10% conditioned media from MDA-MB-435 cells in DMEM/F12 (FIG. 3B). This indicates that the ability of MDA-MB-435 cells to induce osteoclastogenesis in RAW264.7 cells is due to a released factor rather than cell-to-cell contact. MDA-MB-435 also may release an inhibitory factor such as OPG as the number of osteoclasts formed decreased with higher concentrations of conditioned media.

Figures 4A, 4B:
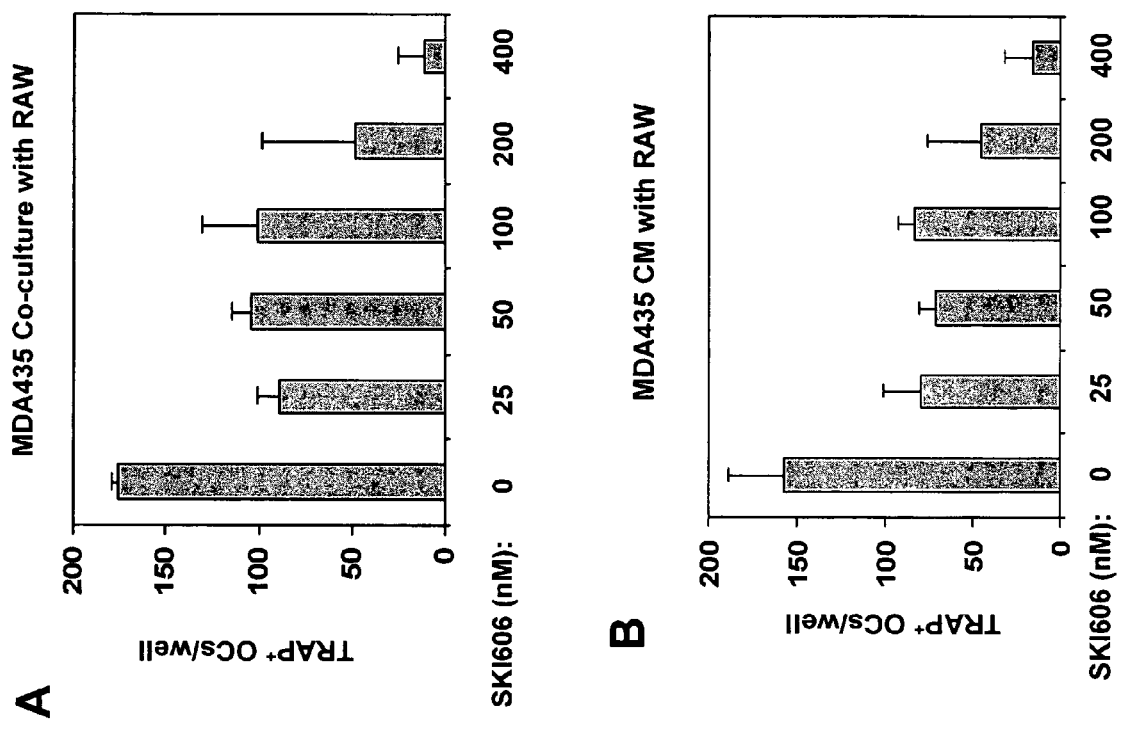
FIGS. 4A-4B. SKI606 inhibits MDA-MB-435 stimulated osteoclastogenesis in RAW264.7.

Additional studies included the investigation of the ability of SKI606 to inhibit breast cancer-induced osteoclast formation. SKI606 significantly inhibited the MDA-MB-435-induced ostoclastogenesis in RAW264.7 cells at a concentration of 400 nM SKI606 (FIG. 4A). SKI606 was also able to inhibit the osteoclastogenesis induced by conditioned media from MDA-MB-435 cells in a dose-dependent manner (FIG. 4B).

Figures 5A, 5B, 5C:
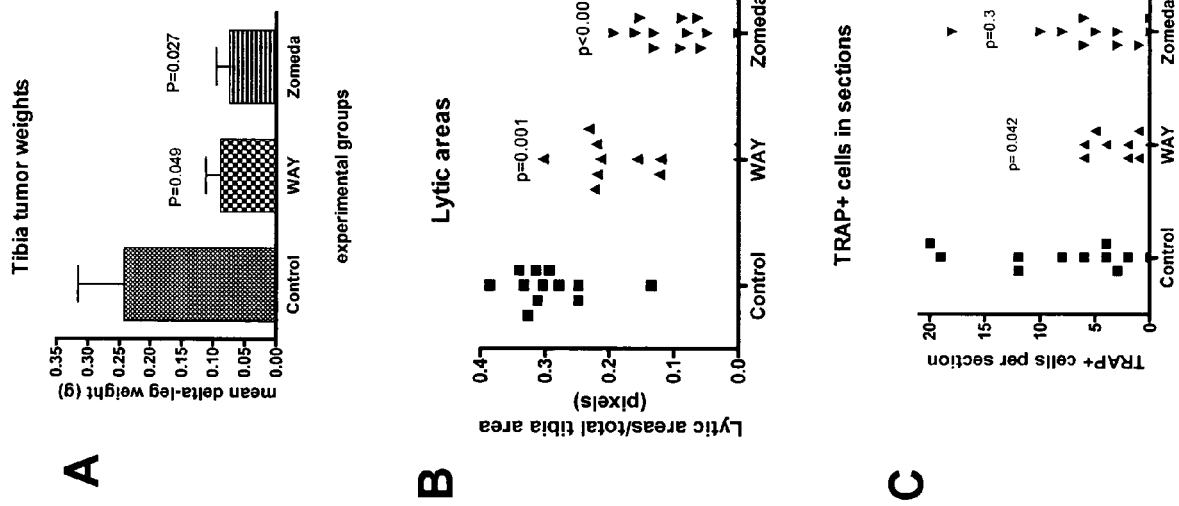
FIGS. 5A-5C. SKI606 significantly decreases tumor growth and osteolytic lesions. Mice were divided into 3 treatment groups. Treatment was initiated 3 days after tibial injection of $5 \times 10^5$ MDA-MB-435 cells of either oral gavage of vehicle (0.5% Methocel/0.4% Tween in PBS), 150 mg/kg SKI606 in vehicle, or S.C. injections of 10 mg/kg Zomeda (zolendronic acid) in 0.1 ml PBS 5 days per week for 9 weeks.
Figure 6A:
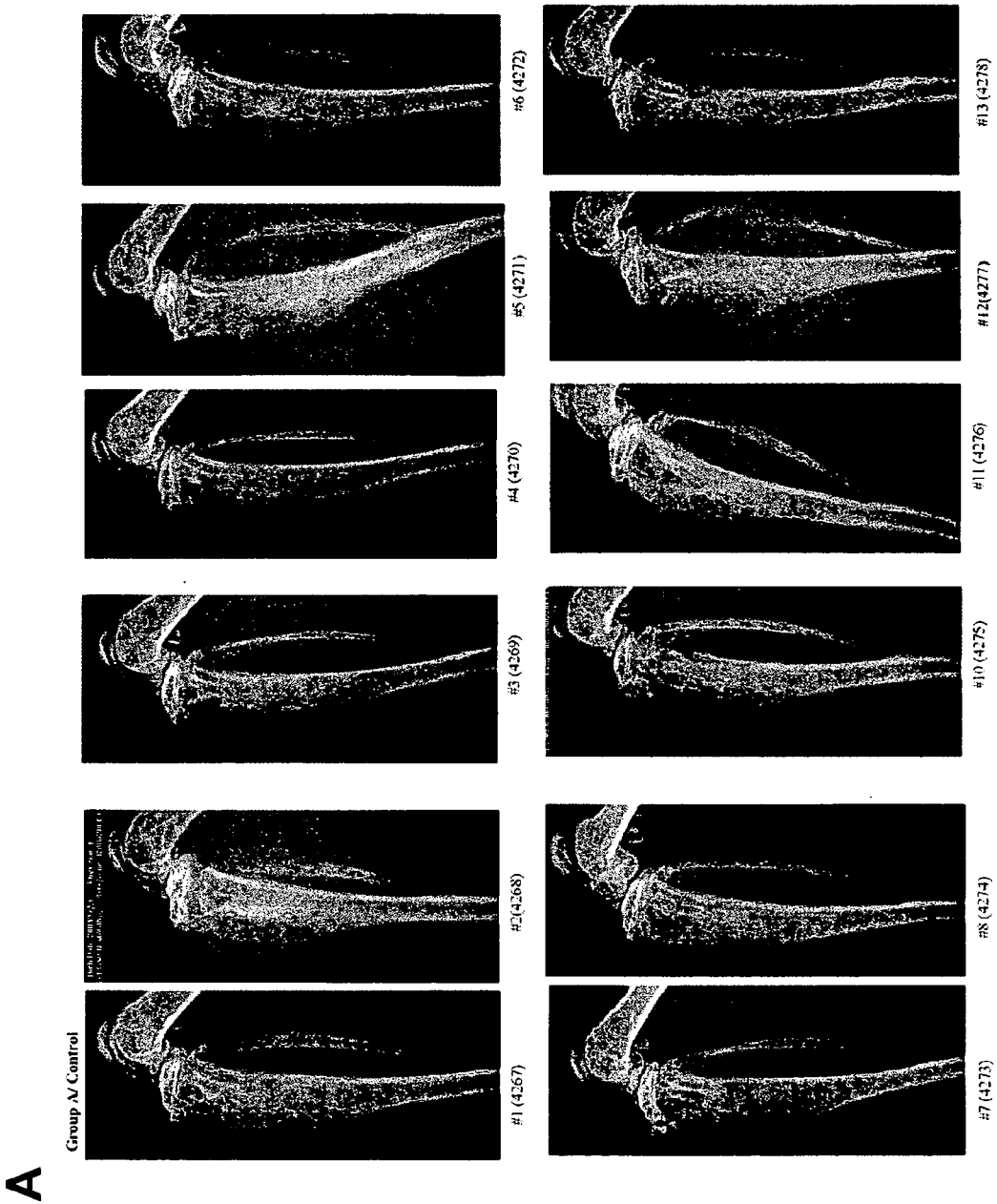
FIGS. 6A-6C. SKI606 significantly decreases tumor growth and osteolytic lesions. X-ray images were taken at 35 days after injection, and also at 14-day intervals. After 9 weeks, final X-ray images were taken of the control group, treated with oral gavage of vehicle (0.5% Methocel/0.4% Tween in PBS) (FIG. 6A), mice treated with 150 mg/kg (FIG. 6B) or Zomeda (FIG. 6C).
Figure 6B:
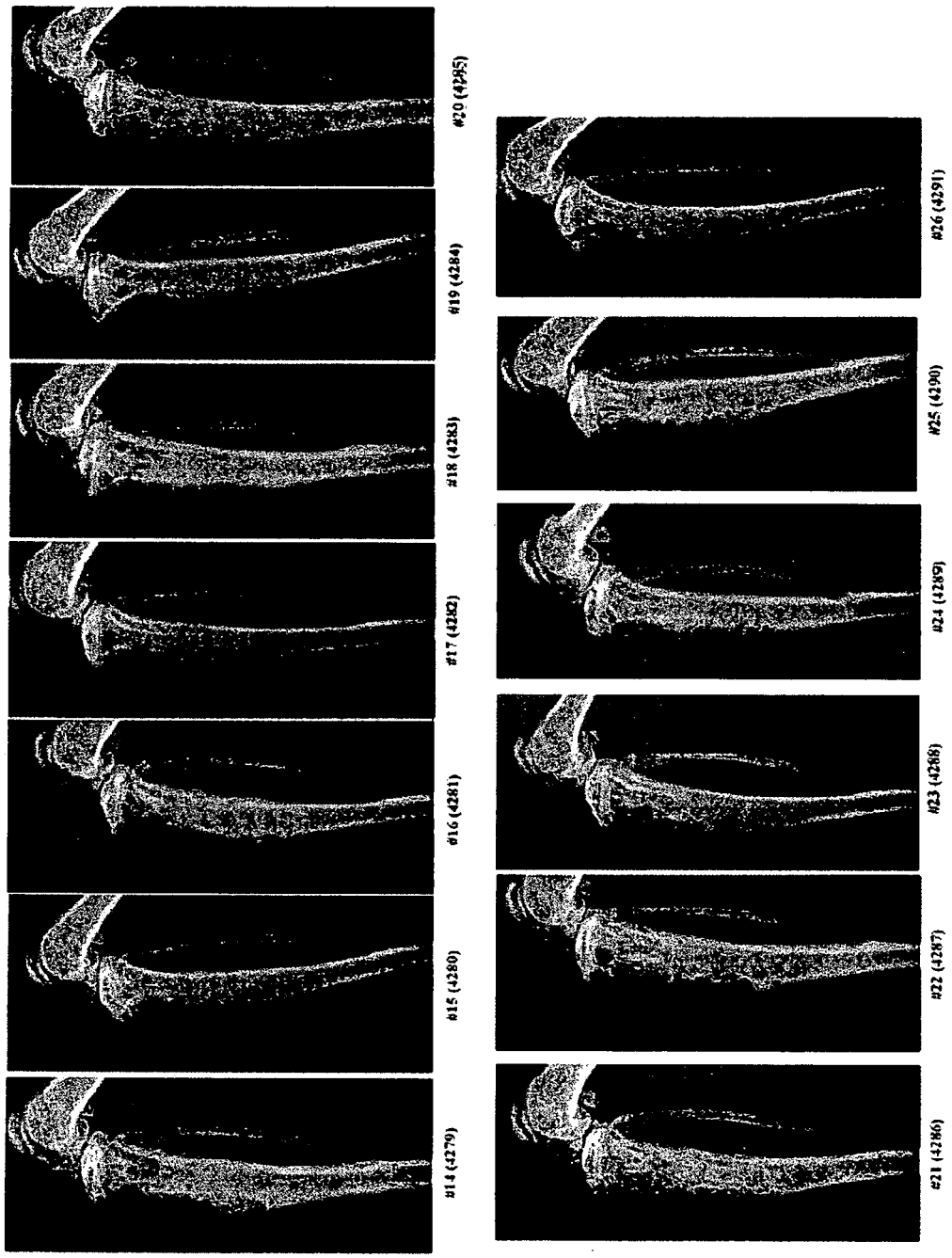
Figure 6C:
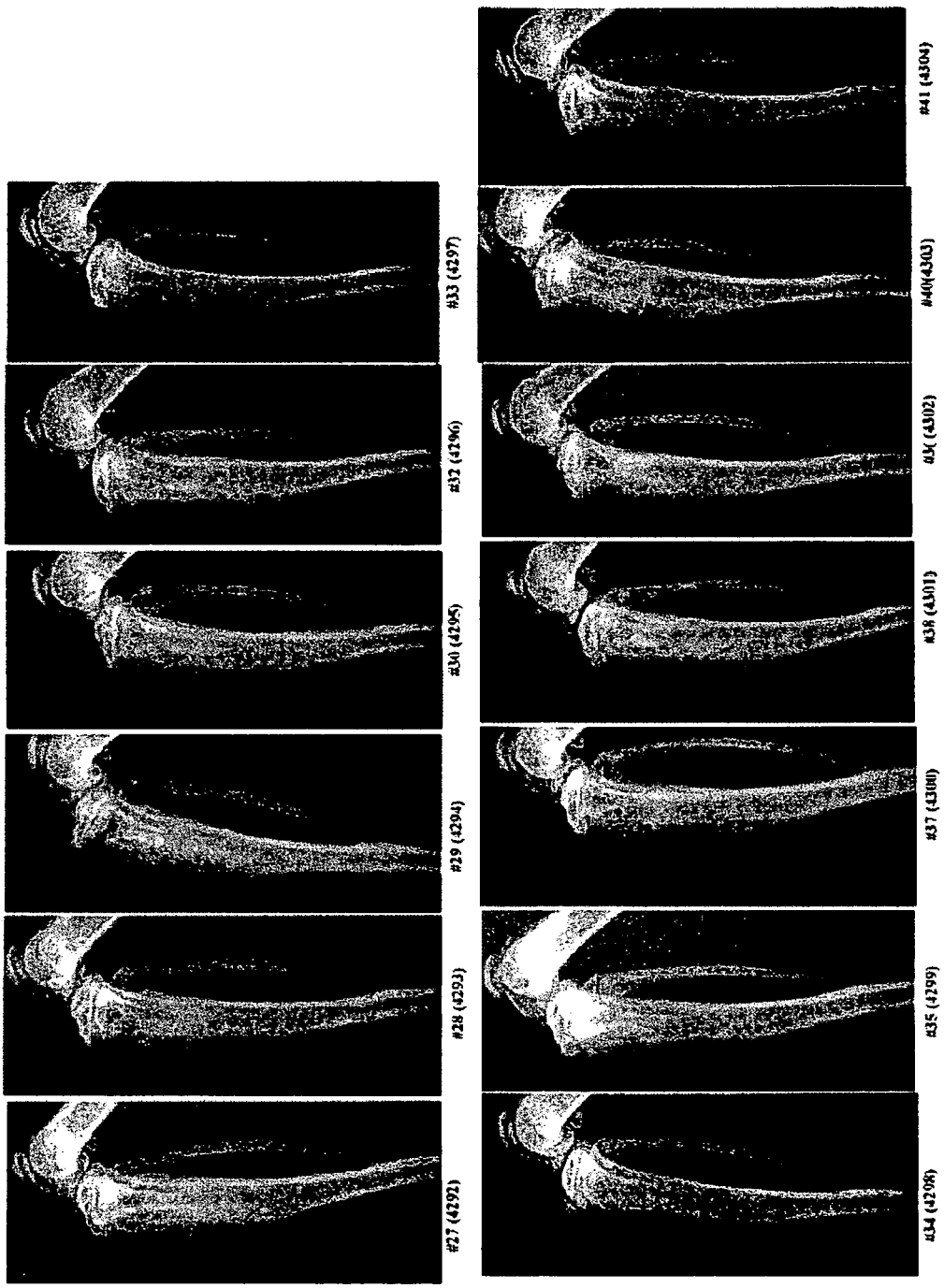

SKI606 was assessed in an in vivo model, using female athymic NCr nude mice (8 weeks old) injected with $5 \times 10^5$ MDA-MB-435 cells in 0.01 ml PBS into the proximal tibia of each mouse using a 28-auge Hamilton needle. Mice were divided into three treatment groups and the incidence of tumor in the tibia was determined by examination of histology sections and weight of tumor. The weights of tibia tumors in mice treated with either SKI606 or Zomeda were significantly smaller than the control group tumors (FIG. 5A and Table 1). Areas of lysis were significantly less in mice treated with SKI606 or Zomeda, (FIG. 5B and Table 1). Furthermore, significantly fewer TRAP-positive cells were counted in sections of tumors from SKI606-treated mice (FIG. 5C). Composites of the digital images are shown in FIGS. 6A-6C.

TABLE 1

Evaluation of SKI606 on MDA-MB-435 Bone Tumor Mouse Model

| Experimental group | Incidence of tumor in tibia | Weight of tumor | Estimate of lytic zones |
| --- | --- | --- | --- |
| Control (vehicle) | 12/12 (100%) | 0.242 +/− 0.07 | 0.294 +/− 0.06 |
| SKI606 | 9/12 (75%) | 0.088 +/− 0.02 | 0.164 +/− 0.09 |
| Zomeda | 11/12 (92%) | 0.073 +/− 0.02 | 0.099 +/− 0.05 |

REFERENCES

The following references, to the extent that they provide exemplary procedural or other details supplementary to those set forth herein, are specifically incorporated herein by reference.

U.S. Pat. No. 4,870,287
U.S. Pat. No. 5,466,468
U.S. Pat. No. 5,760,395
U.S. Pat. No. 6,780,996
U.S. Pat. No. 6,002,008
U.S. Patent Appln, 20050101780A1
Ammann et al., *J. Clin. Invest.*, 99(7):1699-1703, 1997.
Baron et al., *J. Cell Biol.*, 101(6):2210-2222, 1985.
Blair et al., *J. Cell Biol.*, 102(4):1164-1172, 1986.
Blair et al., *J. Cell Biochem.*, 48(4):401-410, 1992.
Blair et al., *J. Cell Biol.*, 102(4):1164-1172, 1986.
Boschelli et al., *Bioorg. Med. Chem. Lett.*, 13:3797, 2003.
Boschelli et al., *J. Med. Chem.*, 44:822, 2001b.
Boschelli et al., *J. Med. Chem.*, 47:1599, 2004.
Bucay et al., *Genes Dev.*, 12(9):1260-1268, 1998.
Dougall et al., *Genes Dev.*, 13(18):2412-2424, 1999.

Franzoso et al., *Genes Dev.,* 11 (24):3482-3496, 1997.
Fujikawa et al., *Ann. Rheum. Dis.,* 55(11):816-822, 1996.
Iotsova et al., *Nat. Med.,* 3(11):1285-1289, 1997.
Johnson et al., *Cell.* 71(4):577-86, 1992.
Kong et al., *Nature,* 397(6717):315-323, 1999.
Lewis et al., *Proc. Natl. Acad. Sci. USA,* 90(24):11618-11622, 1993.
Li et al., *Proc. Natl. Acad. Sci. USA,* 97(4):1566-1571, 2000.
Lomaga et al., *Genes Dev.,* 13(8):1015-1024, 1999.
Mitchell et al., *Ann. NY Acad. Sci.,* 690:153-166, 1993.
Mitchell et al., *J. Clin. Oncol.,* 8(5):856-869, 1990.
Mizuno et al., *Gene,* 215(2):339-343, 1998.
Morton et al., *Arch. Surg.,* 127:392-399, 1992.
Mundy et al., *Cancer,* 80(8 Supply):1546-1556, 1997.
Mundy, *Ann. NY Acad. Sci.,* 593:91-97, 1990.
Poli et al., *EMBO J.,* 13(5): 1189-1196, 1994.
Ravindranath and Morton, *Intern. Rev. Immunol.,* 7: 303-329, 1991.
Remington's Pharmaceutical Sciences, 15*th* ed., pages 1035-1038 and 1570-1580, Mack Publishing Company, Easton, Pa., 1980.
Rickard et al., *J Bone Miner Res.,* 11 (3):312-324, 1996.
Rosenberg et al., *Ann. Surg.* 210(4):474-548, 1989 Boschelli et al., *J. Med. Chem.,* 44:3965, 2001a.
Rosenberg et al., *N. Engl. J. Med.,* 319:1676, 1988.
Scheven et al., *Nature,* 321(6065):79-78, 1986.
Soriano et al., *Cell,* 64(4):693-702, 1991.
Takahashi et al., *Lab Invest.* 74(4):827-34, 1996
Takahashi et al., *J. Bone Miner Res.,* 2(4):311-317, 1987.
Vaes, *J. Cell Biol.,* 39(3):676-697, 1968.
Ye et al., 221 *The National Meeting of the American Chemical Society,* San Diego, Calif. April, 2001.

What is claimed is:

1. A method of inhibiting bone resorption comprising, providing to a subject with pathological bone resorption a therapeutically effective amount of a compound of the formula

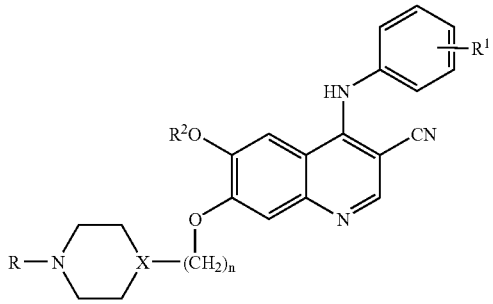

Formula I wherein:
n is an integer from 1-3;
X is N, CH, provided that when X is N, n is 2 or 3;
R is an alkyl of 1 to 3 carbon atoms;
R(1) is 2,4-diCl, 5-OMe; 2,4-diCl; 3,4,5-tri-OMe; 2-Cl, 5-OMe; 2-Me, 5-OMe; 2,4-diMe; 2,4-diMe-5-OMe, 2,4-diCl, 5-OEt;
R(2) is an alkyl of 1 to 2 carbon atoms, or a pharmaceutically acceptable salts thereof.

2. The method of claim 1 wherein the compound is of the formula:

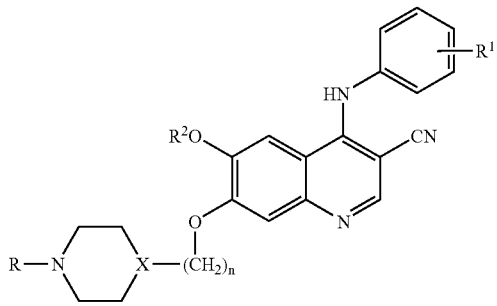

Formula I wherein:
n is an integer from 2-3;
X is N, CH, provided that when X is N, n is 2 or 3;
R is alkyl of 1 to 3 carbon atoms;
R(1) is 2,4-diCl, 5-OMe; 2,4-diCl; 3,4,5-tri-OMe; 2-Cl, 5-OMe; 2-Me, 5-OMe; 2,4-di -Me; 2,4-diMe-5-OMe, 2,4-diCl, 5-GEt;
R(2) is alkyl of 1 to 2 carbon atoms, or a pharmaceutically acceptable salts thereof.

3. The method of claim 1 wherein the compound is of the formula:

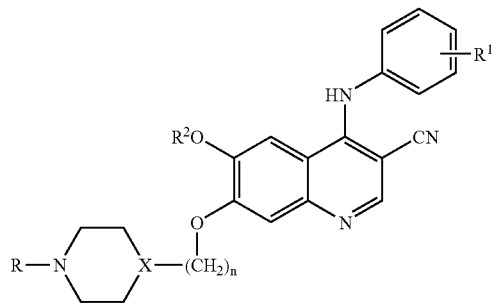

Formula I

X is N, CH
N is 3;
R(2) and R are methyl; or a pharmaceutically acceptable salts thereof.

4. The method of claim 1 wherein R(2) is methyl.
5. The method of claim 1 wherein X is N.
6. The method of claim 1 wherein X is CH.
7. The method of claim 1 wherein the compound is 4-[(2, 4-Dichloro-5- methoxyphenyl)amino]-6-methoxy-7-]3-(4-methyl-1-piperazinyl)propoxy]-3-quinolinecarbonitrile or a pharmaceutically acceptable salt thereof.
8. The method of claim 1 wherein the compound is 4-[(2, 4-Dichloro-5-methoxyphenyl) amino]-7-[3-(4-ethyl- 1-piperazinyl)propoxy]-6-methoxy-3- quinolinecarbonitrile; 4-[(2,4-Dichloro-5-methoxyphenyl)amino]-6-methoxy-7-[2-(4-methyl-1-piperazinyl)ethoxy]-3-quinolinecarbonitrile; 4-[(2,4-Dichloro-5-methoxyphenyl)amino]-7-[2-(4-ethyl-1-piperazinyl)ethoxy]-6-methoxy-3-quinolinecarbonitrile; 4-[(2,4-Dichloro-5-methoxyphenyl)amino]-6-methoxy-7-[(1-methylpiperidin-4-yl)methoxy]-3-quinolinecarbonitrile; 4-[(2,4-Dichloro-5-methoxyphenyl)amino]-6-methoxy-7-[2-(1-methylpiperidin-4-yl)ethoxy]-3-quinolinecarbonitrile; 4-[(2,4-Dichloro-5-methoxyphenyl)amino]-6-methoxy-7-

[3-(1-methylpiperidin-4-yl)propoxy]quinoline-3-carbonitrile; 4-[(2,4-Dichloro-5-methoxyphenyl)amino]-7-[(1-ethylpiperidin-4-yl)methoxy]-6-methoxyquinoline-3-carbonitrile; 4-[(2,4-Dichloro-5-methoxyphenyl)amino]-6-ethoxy-7-[3-(4-methylpiperazin-1-yl)propoxy]quinoline-3-carbonitrile; 4-[(2,4-Dichloro-5-methoxyphenyl)amino[-6-ethoxy-7-]( 1 -methylpiperidin-4-yl)methoxy]quinoline-3-carbonitrile; 4-[(2,4-Dichloro-5-methoxyphenyl)amino]-6-ethoxy-7-[3-(4-ethylpiperazin-1-yl)propoxy]quinoline-3-carbonitrile; 4-[(2,4-Dichloro-5 -methoxyphenyl)amino]-6-ethoxy-7-[3-( 1-methylpiperidin-4-yl)propoxy]quinoline-3-carbonitrile; 4-[(2,4-Dichloro-5-methoxyphenyl)amino]-6-ethoxy-7-[2-(4-methyl- 1-piperazinyl)ethoxy]quinoline-3-carbonitrile; 4-[(2,4-Dichloro-5-methoxyphenyl)amino]-6-ethoxy-7-[2-( 1-methylpiperidin-4-yl)ethoxy]quinoline-3-carbonitrile; 4-[(2,4-Dichloro -5-methoxyphenyl)amino]-6-methoxy-7-[3-(4-propyl- 1-piperazinyl)propoxy]-3quinolinecarbonitrile; 4-[(2,4-dichlorophenyl)amino]-6-methoxy-7-[(1-methylpiperidin -4-yl)methoxy]-3-quinolinecarbonitrile; 6-methoxy-7-[(1-methylpiperidin-4-yl)methoxy]-4-[(3 ,4,5-trimethoxyphenyl)amino]quinoline-3-carbonitrile; 4-[(2-chloro-5-methoxyphenyl)amino]-6-methoxy-7-[(1-methylpiperidin-4-yl)methoxy]quinoline-3carbonitrile; 6-methoxy-4-[(5-methoxy-2-methylphenyl)amino]-7-[(1-methylpiperidin-4-yl)methoxy]quinoline-3-carbonitrile; 4-[(2,4-dimethylphenyl)amino]-6-methoxy-7-[(1-methylpiperidin-4-yl )methoxy]quinoline-3-carbonitrile; 6-methoxy-4-[(5-methoxy-2,4-dimethylphenyl)amino]-7-[(1-methylpiperidin-4-yl)methoxy]quinoline-3-carbonitrile; 4-[(2,4-dichloro-5-ethoxyphenyl)amino]-6-methoxy-7-[(1-methylpiperidin-4-yl)methoxy]quinoline-3-carbonitrile; or pharmaceutically acceptable salt thereof.

9. The method of claim 1 wherein the compound is a Src kinase inhibitor.

10. The method of claim 1, wherein the pathological bone resorption is associated with osteoporosis; giant cell tumor of bone; multiple myeloma; familial expansile osteolysis; osteopenia; periodontal disease; hyperparathyroidism; periarticular erosions in rheumatoid arthritis; Paget's disease; immobilization-induced osteopenia; hypercalcemia of malignancy; bone metastasis; adamantinoma; aneurysmal bone cyst (lesion); angiosarcoma (high grade); angiosarcoma (low grade); bone lesions of Gaucher's disease; Brown tumor of hyperparathyroidism; chondroblastoma; chondromyxoid fibroma; chondrosarcoma; chordoma; clear cell chondrosarcoma; conventional intramedullary osteosarcoma; degenerative joint disease; desmoplastic fibroma; diaphyseal medullary stenosis with malignant fibrous. histiocytoma; enchondroma; eosinophilic granuloma; epithelioid hemangioendothelioma; Ewing's sarcoma of bone; extraosseous osteosarcoma; fibrosarcoma; fibrous dysplasia; florid reactive periostitis; glomus tumor; granulocytic sarcoma in bone; Hardcastle's syndrome; hemangioma; hemangiopericytoma; high-grade surface osteosarcoma; Hodgkin lymphoma of bone; intracortical osteosarcoma; intraosseous well-differentiated osteosarcoma; juxtacortical chondroma; leukemia; malignant fibrous hystiocytoma; melorheostosis; metastatic breast cancer; metastatic kidney cancer; metastatic lung cancer; metastatic prostate cancer; multifocal osteosarcoma; myositis ossificans; neurofibroma of bone; non Hodgkin lymphoma; nonossifying fibroma (fibrous cortical defect); Nora's lesion; osteoblastoma; osteochondroma; osteochondromatosis; osteofibrous dysplasia; osteoid osteoma; osteoma; osteomyelitis; osteopathia striata; osteopoikilosis; parosteal osteosarcoma; periosteal chondroma; periosteal osteosarcoma; pigmented villonodular synovitis; post-paget's sarcoma; schwannoma of bone; small cell osteosarcoma; solitary bone cyst; solitary fibrous tumor; solitary myeloma (plasmacytoma); subchondral cyst; synovial chondromatosis; telangectatic osteosarcoma; "Tug" lesions—metaphyseal fibrous defect; or unicameral bone cyst.

11. The method of claim 10, wherein the bone metastasis is a lung, head and neck, breast, pancreatic, prostate, renal, bone, testicular, cervical, gastrointestinal, colon, bladder cancer metastasis.

12. The method of claim 11, wherein the bone metastasis is a breast or prostate cancer metastasis.

13. The method of claim 11, further comprising providing an anti-neoplastic therapy.

14. The method of claim 13, wherein the anti-neoplastic therapy is chemotherapy, radiotherapy, immunotherapy, or surgery.

15. The method of claim 1, wherein the compound is administered orally.

* * * * *

UNITED STATES PATENT AND TRADEMARK OFFICE
CERTIFICATE OF CORRECTION

PATENT NO. : 7,468,379 B2  
APPLICATION NO. : 11/455272  
DATED : December 23, 2008  
INVENTOR(S) : Bryant G. Darnay et al.

Page 1 of 1

It is certified that error appears in the above-identified patent and that said Letters Patent is hereby corrected as shown below:

In claim 2, column 22, line 23, delete "5-GEt" and insert -- 5-OEt -- therefor.

In claim 3, column 22, line 46, delete "N" and insert -- n -- therefor.

In claim 7, column 22, lines 53-54, delete "methoxy-7-]3-(4-methyl" and insert -- methoxy-7-[3-(4-methyl -- therefor.

In claim 8, column 23, lines 6-7, delete "[-6-ethoxy-7-]" and insert -- ]-6-ethoxy-7-[ -- therefor.

In claim 8, column 23, line 18, delete "3quinolinecarbonitrile" and insert -- 3-quinolinecarbonitrile -- therefor.

In claim 8, column 23, line 24, delete "3carbonitrile" and insert -- 3-carbonitrile -- therefor.

Signed and Sealed this

Seventeenth Day of March, 2009

JOHN DOLL  
*Acting Director of the United States Patent and Trademark Office*